United States Patent [19]

Feinberg et al.

[11] Patent Number: 5,599,680
[45] Date of Patent: Feb. 4, 1997

[54] DIAGNOSTIC APPLICATIONS OF MOUSE ASCITES GOLGI (MAG) MANIPULATION

[75] Inventors: Ronald F. Feinberg, Cherry Hill, N.J.; Harvey J. Kliman, Philadelphia, Pa.

[73] Assignee: The Trustees of the University of Pennsylvania, Philadelphia, Pa.

[21] Appl. No.: 199,551

[22] Filed: Feb. 22, 1994

Related U.S. Application Data

[63] Continuation of Ser. No. 694,926, May 2, 1991, abandoned, which is a continuation-in-part of Ser. No. 587,395, Sep. 25, 1990, Pat. No. 5,276,017, which is a continuation-in-part of Ser. No. 583,034, Sep. 14, 1990, abandoned.

[51] Int. Cl.$^6$ .......................... G01N 33/53; A61B 10/00
[52] U.S. Cl. .......................... 435/7.21; 128/738; 435/806; 436/65; 436/814; 436/906
[58] Field of Search .................... 435/7.21, 806; 436/65, 814, 518, 519, 547, 906; 530/850; 128/738

[56] References Cited

PUBLICATIONS

Arceci et al., "The Gene Encoding Multidrug Resistance is Induced and Expressed at High Levels During Pregnancy in the Secretory Epithelium of the Uterus", *Proc. Natl. Acad. Sci. USA* 85: 4350–4354 (1988).

Axiotis et al., "P–Glycoprotein Expression is Increased in Human Secretory and Gestational Endometrium", *Laboratory Investigation* 65: 577–581 (1991).

Axiotis et al., "Rapid Communication: Immunohistochemical Detection of P–Glycoprotein in Endometrial Adenocarcinoma", *Amer. J. of Pathology* 138: 799–806 (1991).

Finstad et al., "Some Monoclonal Antibody Reagents (C219 and JSB–1) to P–Glycoprotein Contain Antibodies to Blood Group A Carbohydrate Determinants: A Problem of Quality control for Immunohistochemical Analysis", *J. Histochemistry and Cytochemistry* 39: 1603–1610 (1991).

Smith et al., "Endogenous and monoclonal Antibodies to the Rat Pancreatic Acinar Cell golgi Complex," *J. Cell Biol* 98: 2035–2046 (1984).

Thiebaut et al., "Cellular Localization of the Multidrug–Resistance Gene Product P–Glycoprotein in Normal Human Tissues", *Proc. Natl. Acad. Sci. USA* 84: 7735–7738 (1987).

Kliman et al, 1995. A Mucin–Like Glycoprotein Identified by MAG (Mouse Ascites Golgi) Antibodies. Menstrual Cycle–Dependent Localization in Human Endometrium Am J Pathol 146:166–181.

*Primary Examiner*—Christina Y. Chan
*Assistant Examiner*—James L. Grun
*Attorney, Agent, or Firm*—Woodcock Washburn Kurtz Mackiewicz & Norris

[57] ABSTRACT

Therapeutic and diagnostic applications by the detection and manipulation of mouse ascites golgi factor produced by endometrium and present in other exocrine tissues and defined by an antibody found in mouse ascites are provided by this invention.

1 Claim, 2 Drawing Sheets

DIAGNOSTIC APPLICATIONS OF MOUSE ASCITES GOLGI (MAG) MANIPULATION

CROSS REFERENCE TO RELATED APPLICATIONS

This is a continuation, of application Ser. No. 07/694,926, filed May 2, 1991 now abandoned, which application is a continuation-in-part of application U.S. Ser. No. 587,395 filed Sep. 25, 1990, now U.S. Pat. No. 5,276,017, which application is a continuation-in-part of U.S. Ser. No. 583,034 filed Sep. 14, 1990, now abandoned.

FIELD OF THE INVENTION

The present invention relates to the field of mammalian diagnostics and therapeutics. In particular, the invention relates to therapeutic and diagnostic applications through the identification of the factor, mouse ascites golgi factor (MAG). More particularly, therapeutic and diagnostic applications relating to fertility enhancement, contraception and contragestion are provided.

BACKGROUND OF THE INVENTION

In the field of mammalian reproduction, many diagnostic procedures exist to aid the reproduction practitioner in making a diagnosis and choosing an appropriate course of action.

Currently, infertility in humans is defined as one year of unprotected coitus without conception. Approximately 10–15% of couples are affected by infertility. The risk of infertility is doubled for women between the ages of 35 to 44 as compared to women between the ages of 30 and 34. Approximately 600,000 couples sought professional help during the year 1968. However, in the early 1980's this number increased to over 2 million visits per year for infertility. Changes in fertility patterns will have a significant impact on the make-up of populations. It has been calculated that by the middle of the next century, the population in the United States will decline without immigration. Furthermore, the percent of people over the age of 65 will increase to over 23% in the next 100 years, resulting in an older and smaller work force.

In the United States, the majority of infertility can be accounted for by problems in the female. Evaluating a female for infertility can be complex. Examination of the fallopian tubes is an important early step in mammalian fertility evaluation due to the increased evidence of pelvic inflammatory disease. Currently, a hysterosalpingogram (HSG) is the procedure of choice to examine the patency of the fallopian tubes. In addition to HSG, hysteroscopy which is the direct examination of the uterus by a fiber optic device, is important to determine the presence of endometrial polyps, submucous leiomyomas, and other abnormalities within the uterus itself.

Another category of diagnostic procedures includes examination of ovarian function including ovulation and the secretion of progesterone during the luteal phase of the menstrual cycle. Ovarian function can be crudely assessed by measuring basal body temperatures during the menstrual cycle and cervical mucous testing around the time of ovulation. More accurate testing can be performed by measuring luteinizing hormone, a pituitary hormone which induces ovulation after a mid-cycle surge. Finally, serum progesterone levels can be measured to assess for normal luteal phase of the menstrual cycle.

The endometrium itself can be directly assessed by performing an endometrial biopsy three days before the suspected onset of menses. In assessing a mammalian endometrium, current gynecology and infertility physicians depend on pathologists to examine endometrial biopsies by hematoxylin and eosin staining of paraffin embedded specimens. For infertility patients, the reading of these biopsies provides information about the day of the cycle following ovulation, the adequacy of the luteal phase, and other potential data, such as infection, inflammation, or neoplasia of the endometrium. However, in most cases there is no evaluation of the functional and biochemical quality of the endometrium, and often no histologic reading to explain a patient's infertility problem.

Finally, the infertility patient could undergo endoscopic examination through an incision in the abdomen to directly visualize the external surfaces of the ovary, fallopian tubes and uterus to visualize any gross pathology which was not detected by previous examinations.

A high percentage of women who are unable to carry a pregnancy to full term undergo spontaneous abortion generally within the first six weeks. Pregnancy loss during the first six weeks has been shown to be as high as between 15 and 20%. Furthermore, the chance of a successful live birth after consecutive abortions without a live birth is only 40–50%.

In vitro fertilization (IVF) requires the removal of ova from a mammalian ovary, and exposure of these ova to sperm outside the body. Fertilization of each ovum requires that at least one living sperm penetrates the zona pellucida (outer covering) of the ovum and fuses with the pronucleus. Once this has occurred and the ova are fertilized, they can be transferred to a uterus where they can become implanted on the uterine wall. If implantation occurs, the pregnancy can proceed as if fertilization had occurred within the body. In vitro fertilization has gained widespread professional and public acceptance. However, despite the ever increasing frequency and refinement of this procedure, in vitro fertilization attempts most often do not result in pregnancy. In vitro pregnancy rates are currently only about 15 to 20 percent. For a variety of reasons, exposing the ova to sperm does not necessarily result in fertilization. Furthermore, even where the ova is fertilized, the placement of the ova in a uterus usually does not result in normal implantation. The low success rate of IVF often leads to an excessive financial and psychological burden for the infertile couple.

Other assisted reproductive technologies include two modifications of the IVF technique. The first is gamete intra-fallopian transfer (GIFT), the second is zygote intra-fallopian transfer (ZIFT). In the GIFT procedure, the retrieved oocyte and sperm are mixed together and placed back into the fallopian tube where fertilization takes place. The fertilized zygote then travels down through the fallopian tube into the endometrial cavity, where implantation may or may not take place. The ZIFT procedure allows for fertilization to take place in vitro as in standard IVF, and then the fertilized zygote is placed back in the fallopian tube where it then travels down into the uterus to implant. Finally, it is becoming realized that the hyper-stimulation protocols necessary to retrieve many oocytes from the donor woman may have deleterious effects on the endometrium itself and decrease the rates of implantation. Two basic procedures have been utilized to help overcome this problem. The first is considered non-stimulated oocyte retrieval. A single egg is retrieved, allowed to be fertilized and placed back into the fallopian tube or uterus for implantation. The other technique involves the hyper-stimulation portion of the IVF procedure to retrieve the eggs and allow for fertilization in vitro. The zygotes are then frozen to be placed back into the patient after several normal cycles, with the hope that the endometrium will be more receptive to implantation. All of these techniques attempt to maximize the quality of the eggs, zygotes produced after fertilization and the receptivity of the endometrium. Any procedure which would enhance the implantation rate above the standard 15 to 20% would have a marked positive effect on any of these technologies.

There has been reported antibodies directed specifically to the Golgi complex. Smith et al., "Endogenous and monoclonal antibodies to the rat pancreatic acinar cell golgi complex", *The Journal of Cell Biology*, 98:2035–2046 (1984). Smith et al. disclosed immunofluorescence of tissue sections reacted with normal mouse serum demonstrated an antibody in the serum that localized to the Golgi complex area of the rat pancreatic acinar cell. The antibody is disclosed to be of IgG classes and the antigen to be an integral membrane component of the of the Golgi complex. Monoclonal antibodies (MAbs) were prepared by the authors and one MAb revealed an antigen of from about 103 to about 108 kd and the other MAb bound to two bands of 180 kd and 103 to 108 kd. The antigens are believed by the authors to be proteins.

SUMMARY OF INVENTION

There is provided by the invention a novel method of diagnosing the relative receptivity of the endometrium of a mammal to implantation of a conceptus, comprising: sampling the endometrium; and assaying the biopsy for mouse ascites golgi factor, whereby relatively greater concentrations of mouse ascites golgi factor are indicative of a higher probability of receptivity of the endometrium of said mammal to said implantation of a conceptus.

Further provided by the invention is a novel method of diagnosing the relative receptivity of the endometrium of a mammal to implantation of a conceptus, comprising: providing a sample of at least one reproductive fluid from the mammal; and assaying the sample for mouse ascites golgi factor, whereby relatively greater concentrations of mouse ascites golgi factor are indicative of a higher probability of receptivity of the endometrium of said mammal to said implantation of a conceptus.

Further provided by the invention is a novel infertility screening test comprising: assaying at least one bodily fluid or cell type from a mammal suspected of being infertile for the presence of mouse ascites golgi factor autoantibodies.

Further provided by the invention is a novel method of increasing the probability that a conceptus will become implanted in a mammalian uterus comprising the step of: infusing mouse ascites golgi factor into the uterine cavity at about the time the uterus is expected to be contacted with an ovum or said conceptus, said infusing introducing a sufficient amount of mouse ascites golgi factor onto the surface of the uterine cavity to increase the probability that implantation will occur.

Further provided by the invention is a novel method of increasing the success rate of assisted reproductive technologies comprising the steps of: contacting a mammalian ovum or conceptus with a sufficient amount of mouse ascites golgi factor prior to introduction of said ovum or conceptus into the reproductive tract of a female mammal.

Further provided by the invention is a novel method of augmenting mouse ascites golgi factor synthesis in a mammal comprising administering to the mammal an agent which stimulates mammalian endometrial cells in culture to make mouse ascites golgi factor in an amount effective to augment mouse ascites golgi factor synthesis in the mammal.

Further provided by the invention is a novel method of increasing the probability that a conceptus will become implanted in a mammalian uterus comprising the step of: administering to the mammal an agent which stimulates mammalian endometrial cells in culture to make mouse ascites golgi factor at about the time the uterus is expected to be contacted with said conceptus, in an amount effective to increase the probability that implantation will occur.

Further provided by the invention is a novel method of inhibiting mouse ascites golgi factor synthesis in mammal comprising administering to said mammal a compound which inhibits mouse ascites golgi factor synthesis by mammalian endometrial cells in culture in an amount effective to inhibit mouse ascites golgi factor synthesis in said mammal.

Further provided by the invention is a novel method of contraception comprising administering to a mammal a compound which inhibits mouse ascites golgi factor synthesis by mammalian endometrial cells in culture in an amount effective to increase the probability that conception will be prevented in said mammal.

Further provided by the invention is a novel method of contragestion comprising administering to a mammal a compound which inhibits mouse ascites golgi factor synthesis by mammalian endometrial cells in culture in an amount effective to increase the probability that contragestion will be effected in said mammal.

Further provided by the invention is a novel method of decreasing free MAG in a mammal comprising administering to said mammal MAG antibodies sufficient to bind to at least some MAG in said mammal.

Further provided by the invention is a novel method of contraception comprising administering to a mammal mouse ascites golgi factor antibodies in an amount sufficient to increase the probability that conception will be prevented in said mammal.

Further provided by the invention is a novel method of contragestion comprising administering to a mammal mouse ascites golgi factor antibodies in an amount sufficient to increase the probability that contragestion will be effected.

Further provided by the invention is a novel method of sterilizing a mammal comprising administering to the mammal a mouse ascites golgi factor antigen in an amount sufficient to raise antibodies to mouse ascites golgi factor, whereby the probability that a conceptus will become implanted in the uterus of the mammal is decreased.

Further provided by the invention is a novel method for producing mouse ascites golgi factor in vitro comprising: culturing mammalian endometrial cells for a time sufficient to produce at least some mouse ascites golgi factor and separating the mouse ascites golgi factor thus produced.

Further provided by the invention is a novel pharmaceutical composition comprising mouse ascites golgi factor in a pharmaceutically acceptable carrier.

Further provided by the invention is a novel substantially purified mammalian mouse ascites golgi factor.

Further provided by the invention is a novel isolated DNA sequence encoding mouse ascites golgi factor.

Further provided by the invention is a novel recombinant expression vector containing a DNA sequence encoding mouse ascites golgi factor wherein the vector is capable of expressing the mouse ascites golgi factor in a host cell.

Further provided by the invention is a novel host cell transformed with the DNA encoding the mouse ascites golgi factor or a portion thereof sufficient for the expression of said mouse ascites golgi factor by said host cell.

Further provided by the invention is a novel method of producing mouse ascites golgi factor which comprises culturing recombinant host cells transformed with a DNA sequence coding for said mouse ascites golgi factor operably linked to appropriate regulatory control sequences which sequences are capable of effecting the expression of said coding sequence in said transformed cells and recovering said expressed mouse ascites golgi factor.

Further provided by the invention is a novel method of using antibodies derivable from mouse ascites which bind to normal mammalian endometrium at about the time the mammal is expected to ovulate to detect mouse ascites golgi factor in a mammal.

Further provided by the invention is a novel method of assessing the secretory function of a mammalian exocrine tissue comprising: providing a sample of the tissue; and assaying the tissue for mouse ascites golgi factor, whereby relatively greater concentrations of mouse ascites golgi factor in the tissue are indicative of a relatively greater secretory function of the tissue.

Further provided by the invention is a novel method of assessing the secretory function of a mammalian exocrine tissue comprising: providing a sample of fluid secreted from the tissue or fluid which had been in contact with the tissue; and assaying the fluid for mouse ascites golgi factor, whereby relatively greater concentrations of mouse ascites golgi factor in the fluid are indicative of a relatively greater secretory function of the tissue.

Surprisingly, the importance of mouse ascites golgi factor in critical phases of mammalian reproduction has been recognized. Accordingly, this invention enhances fertility and provides methods of contraception and provides methods of diagnosis by the manipulation of mouse ascites golgi factor.

Furthermore, it has been recognized that MAG reactivity as demonstrated by immunohistochemistry is present in a variety of other tissues in the human body. These tissues consist mostly of a number of tissues which are part of the exocrine glands (glands which secrete products into ducts) of the body. Thus, MAG is believed to represent a marker of secretory function in these cells. Hence, cells which contain normal MAG reactivity (i.e., staining of the Golgi of a particular cell) would be considered to be a normal secretory cell.

BRIEF DESCRIPTION OF THE DRAWINGS

FIGS. 1A–D are diagrams depicting the patterns of immunohistochemical staining of human endometrium utilizing anti-mouse ascites golgi factor antibody as a function of time during the menstrual cycle. FIG. 1C depicts endometrium at Day 16 of the menstrual cycle. FIG. 1D depicts endometrium at Day 17 of the menstrual cycle. Normal early proliferative endometrium does not show mouse ascites golgi factor staining. The first mouse ascites golgi factor staining is observed at approximately day 8–9. Examination of mid-late proliferative endometrium reveals that virtually all glands and surface epithelium has mouse ascites golgi factor reactivity in normal patients. At day 16, when subnuclear vacuoles are first forming, the mouse ascites golgi factor reactivity begin to spread towards the apical portion of the endometrial glandular cells, suggesting movement of mouse ascites golgi factor within secretory vesicles on their way to being secreted. By day 17—the day of maximal glandular secretion as measured by subnuclear vacuoles—much of the mouse ascites golgi factor reactivity has been secreted out of the glandular cells and into the lumens of the endometrial glands. At this time, the first surface staining of the surface epithelium can be identified. Surface staining continues until day 18. After day 18, little to no mouse ascites golgi factor can be identified anywhere within the endometrium.

DETAILED DESCRIPTION OF THE INVENTION

Figure 1A:
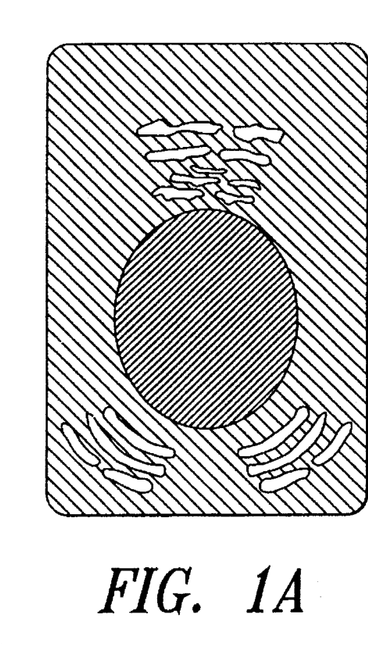
FIG. 1A depicts normal early proliferative endometrium.
Figure 1B:
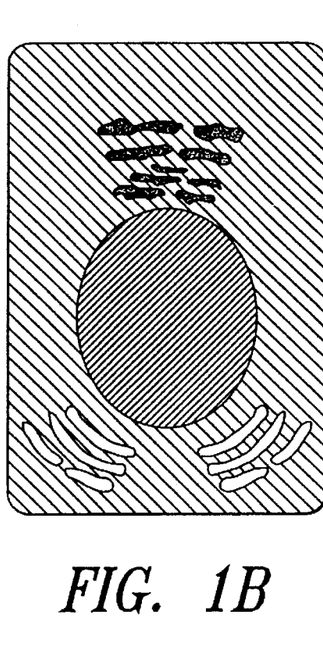
FIG. 1B depicts mid-late proliferative endometrium.
Figure 1C:
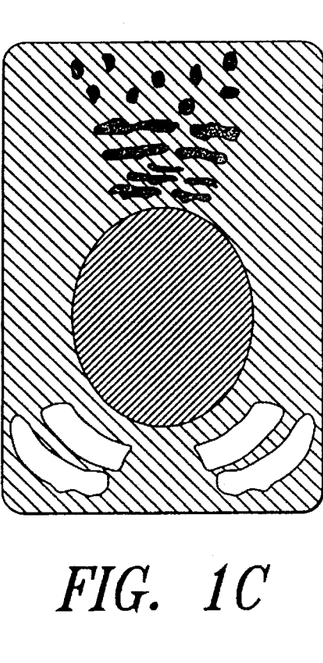
Figure 1D:
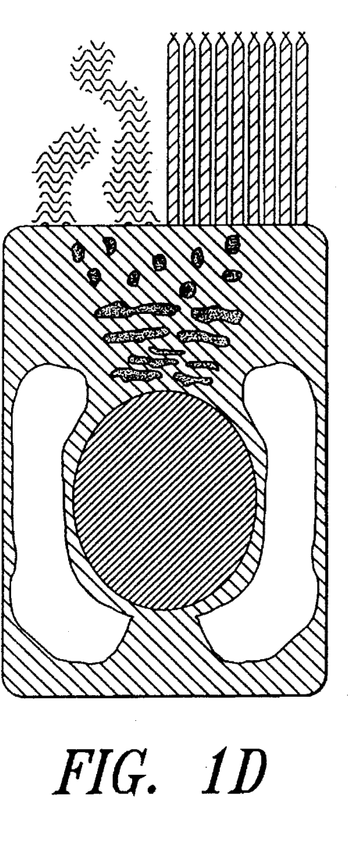
Figure 2:
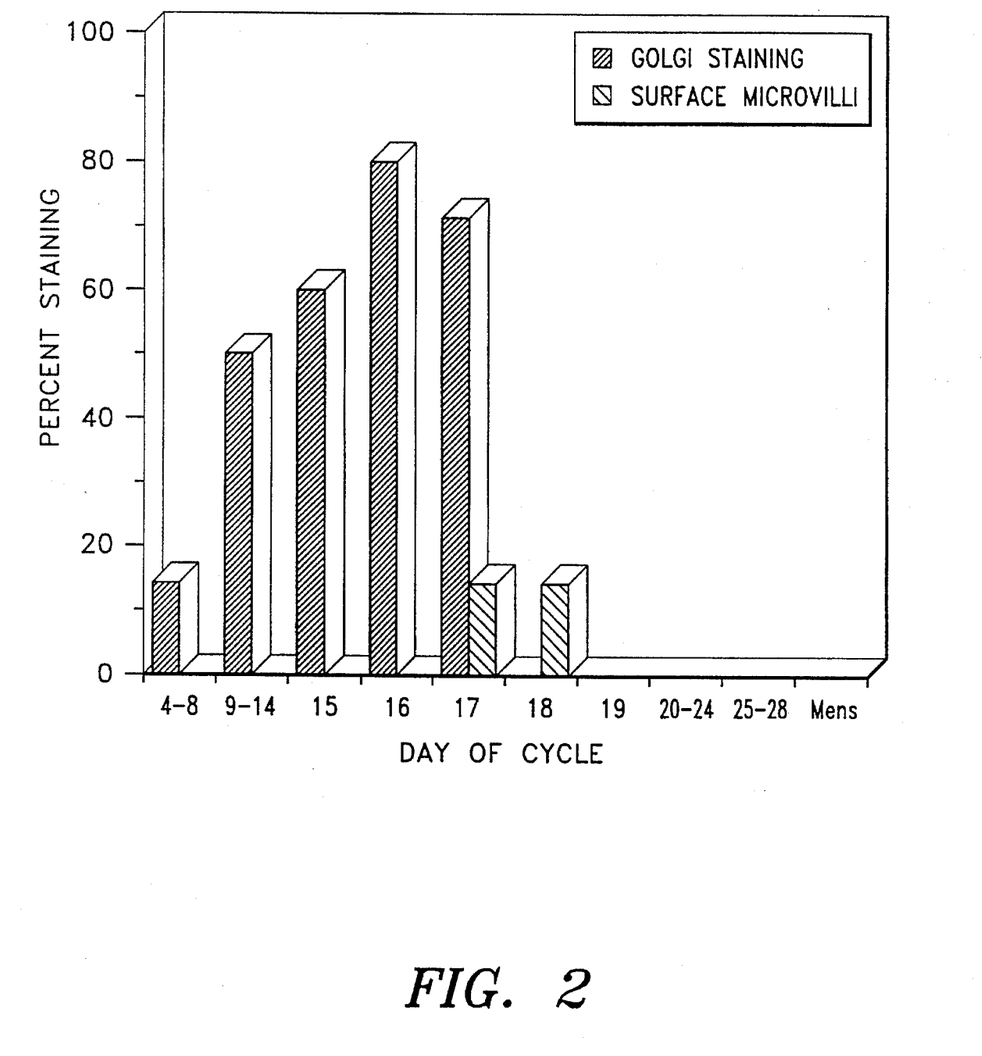
FIG. 2 is a graph depicting percent ascites staining of human endometrium versus the day of menstrual cycle.

"Mouse Ascites Golgi factor" (MAG) as used herein refers to a factor, and fragments thereof, produced by normal mammalian endometrium at around the time the mammal is expected to ovulate, i.e. critical times and locations of reproduction, which factor has been demonstrated to bind to endogenous antibodies found in normal mouse ascites. MAG is also believed to be present in a variety of other mammalian tissues, in particular, tissues which are part of the exocrine glands. Staining of bound antibody to MAG appears in a perinuclear and apical pattern in epithelial cells of the mammalian endometrium, suggesting Golgi and secretory vesicle staining. Furthermore, staining has been demonstrated both within the glands of the endometrium, and within the surface epithelium, where implantation is believed to occur. MAG is believed to be a proteinacious substance.

The antibody which MAG has been shown to bind to is also believed to be found in other biological fluids of a normal or immunized mouse such as serum or plasma and may be found in other animals as well. Thus, mouse ascites is expected to be a suitable source of the antibody for use in the present invention as are other MAG antibodies such as monoclonals made against pure MAG.

The term "Conceptus" as used herein refers to the sum of derivatives of a fertilized ovum at any stage of development from fertilization to birth, including extraembryonic membranes as well as the embryo or fetus.

DIAGNOSIS

A method is provided for diagnosing the relative receptivity of the endometrium of a mammal to implantation of a conceptus, comprising the steps of sampling the endometrium and assaying the biopsy for MAG, whereby relatively greater concentrations of MAG are indicative of a higher probability of receptivity of the endometrium of said mammal to said implantation of a conceptus.

Sampling can conveniently be accomplished with an endometrial biopsy which is performed by a variety of techniques known to those skilled in the art.

The sample can be assayed for the presence of MAG by any method that detects MAG or the messenger RNA coding for MAG. Such assays include an assay wherein the biopsied cells are contacted with a detectably labeled MAG antibody and the labeled antibody coupled to MAG in the sample is detected. The detectable label is conveniently selected from the group consisting of enzymes, chromophores, fluorophores, coenzymes, chemiluminescent materials, enzyme inhibitors, paramagnetic metals and radionucleotides.

An assay also expected to be suitable for use in the present invention is an in situ hybridization assay comprising the steps of contacting the biopsied endometrium with a labeled oligonucleotide probe, specific for MAG messenger RNA, and detecting the labeled oligonucleotide probe coupled to mRNA in the sample. General procedures for in situ hybridization are as described for example in Stroop et al., "Localization of herpes simplex virus in the trigeminal and olfactory systems in the mouse central nervous system during acute and latent infections by in situ hybridization," *Lab. Invest.* 51:27–38 (1984).

Accordingly, the method of this invention, markedly enhances the information gathered from endometrial biopsies by actually assessing whether the mammal is making MAG at the appropriate time in the menstrual cycle and in adequate amounts. In other words, reduced levels of MAG as compared to fertile controls or no MAG levels at all, allows the practitioner to conclude that the mammal is likely to be infertile. Thus, for mammals undergoing assisted reproductive technologies, the method of this invention can provide information on MAG production by the endometrium. Mammals producing suboptimal amounts of MAG as compared to fertile controls, can undergo MAG infusion or augmentation therapy as described below. Alternatively e.g., the time of peak MAG production in the endometrium as determined by a daily biopsy throughout a menstrual cycle, can be selected as the time for contact with a conceptus. Thus, the method of this invention provides information about endometrial receptivity to a conceptus thereby enhancing the probability that a conceptus will be implanted in a uterus. In addition to assessing qualitatively the amount of MAG made in endometrial biopsies, computer image analysis can be utilized to quantitate the amount of MAG made per glandular cell or glandular group or per whole endometrium to give a semi-quantitative estimate of overall fertility potential of the mammal being assessed.

Further provided by this invention, is a method of diagnosing the relative receptivity of the endometrium of a mammal to implantation of a conceptus, comprising the steps of providing a sample of at least one reproductive fluid from the mammal and assaying the sample for MAG, whereby relatively greater concentrations of MAG in the reproductive fluid are indicative of a higher probability of receptivity of the endometrium of said mammal to said implantation of a conceptus.

In non-pregnant females, an assay of reproductive fluids is expected to be a useful indicator of MAG secreted by the mammal, and in particular, by the endometrium. An example of a suitable reproductive fluid would include a cervicouterine aspirate sample. Such an aspirate can be obtained by aspirating secretions from around the cervix and uterus with a syringe.

Assays for MAG are the same as described above.

As with the method to assay the endometrium for MAG described above, it is expected to be useful to assay at least one reproductive fluid at least daily during the menstrual cycle to aid in assisted reproductive technologies. Additionally, measurement of secreted MAG in reproductive fluids is expected to be an important diagnostic test for predicting adequate versus suboptimal amounts of the important implantation protein, MAG. Females with abnormal levels of MAG, as compared with fertile controls, diagnosed by these methods can then be candidates for MAG therapy or pharmacologic manipulations to modulate MAG synthesis, as described in detail below.

The methods of this invention, wherein MAG is assayed in endometrium and reproductive fluids of females are then generally expected to be useful as diagnostic screens for mammals suspected of being infertile. Further, these assays have important applicability for mammals undergoing assisted reproductive technologies in more precisely defining optimal times to attempt fertilization. Currently there is no adequate diagnostic tool to measure the window of endometrial receptivity to a conceptus. These methods of detecting the presence of MAG in reproductive fluids of non-pregnant females or in endometrial biopsies, permit transfer of fertilized or unfertilized ova to the uterine cavity or fallopian tube at an optimal time of endometrial receptivity as judged by MAG levels in normal fertile controls. Such assays are expected to be easy, non-invasive ways to assess levels of MAG in mammals.

In another aspect of this invention, an infertility screening test is provided. At least one bodily fluid or cell type from a mammal suspected of being infertile is assayed for the presence of MAG antibodies.

Conveniently, the presence of antibodies, i.e. anti-MAG antibodies endogenous to the mammal that bind to MAG can be assayed by, for example, basic enzyme-linked immunoassay (ELISA) (where purified MAG is immobilized on a plastic surface, and the subject's bodily fluid, e.g., serum or cervicouterine secretion, is applied to these wells in various dilutions), or immunoblot techniques. A positive test would occur by using a marker secondary anti-human antibody, which would only bind in the assay if the patient's bodily fluids contained an anti-MAG autoantibody.

Bodily fluids expected to be useful include, e.g., plasma, serum and cervicouterine aspirates. Examples of cell types expected to be useful include an endometrial biopsy. Generally, any bodily fluid or cell type associated with MAG in a fertile control are believed to be useful.

Certain causes of previously unexplained infertility are believed due to an autoimmune process leading to endogenous production of anti-MAG antibodies. In one aspect, this autoimmune process is believed to prevent the proper biological function of MAG, thus preventing implantation initially or leading to repetitive miscarriage later in pregnancy.

There is clear precedence for autoimmune infertility. It has been shown that patients who have general autoimmune diseases have a high incidence of reproductive failure. Gleicher N, el RA. (1988) "The reproductive autoimmune failure syndrome," *Am J Obstet Gynecol* 159:223–7

The first step in treating mammals with autoimmune infertility is a screening method to identify this group. Once identified, these patients might benefit from specific treatments used for patients with autoimmune diseases, such as immunosuppressive therapy.

FERTILITY ENHANCEMENT

In another aspect of this invention, a method of increasing the probability that a conceptus will become implanted in a mammalian uterus is provided. By the method of this invention, MAG is infused into the uterine cavity at about the time the uterus will be contacted with a conceptus, said infusing introducing a sufficient amount of MAG onto the surface of the uterine cavity to increase the probability that implantation will occur.

The time a uterus will be contacted with a conceptus can be e.g., at about the time of presumed implantation during a natural cycle of conception, or the time of assisted reproductive technologies. During assisted reproductive technology, MAG could be applied to the uterine cavity either prior to, during, or after the introduction of the fertilized or unfertilized ovum to the uterus or fallopian tube. Alternatively, the method comprises contacting an ovum or conceptus with a sufficient amount of MAG prior to introduction of said ovum or conceptus into a female mammalian reproductive tract, to increase the success rate of assisted reproductive technologies.

MAG could be utilized in a variety of ways as are other agents for introduction into the uterus. For example, MAG could be in a dissolved form, either in solution, within a gel, or in a slow release intrauterine device to allow for an appropriate time-dependent concentration in the uterine cavity.

A sufficient amount of MAG is that amount of MAG which when introduced onto the surface of the uterine cavity or contacted with an ova or conceptus, increases the probability that implantation of a conceptus will occur or increases the success rate of assisted reproductive technologies. The method of the invention is believed to change the local environment of the surface of the endometrium sufficiently to improve the chance of conceptus implantation.

Literature is known describing intrauterine infusions, gels or sponges for the treatment of a variety of conditions. It has been shown that the endocrine function of an ovary could be markedly changed by an intrauterine infusion. Helmer et al. "Intrauterine infusion of highly enriched bovine trophoblast protein-1 complex exerts an antiluteolytic effect to extend corpus luteum life span in cyclic cattle," *J Reprod Fertil* 87:89–101 (1989). It has been shown that rat uteri which received an intrauterine injection of luteinizing releasing hormone had a significantly increased rate of implantation compared to uteri which had no injection. Jones, R. C. "Blastocyst attachment in the ovariectomized rat treated with an intrauterine injection of luteinizing hormone-releasing hormone (LRH)," *Acta Endocrinol* (Copenh) 103:266–8 (1983). In addition to the use of solutions, there are references citing use of gels which are instilled intracervically to facilitate labor and delivery. See e.g., Ekman et al., "Intracervical instillation of PGE2-gel in patients with missed abortion or intrauterine fetal death," *Arch Gynecol* 233:241–5 (1983) Finally, an intrauterine vehicle either similar to those currently existing on the market or modified to facilitate slower release of a pharmacologic agent which might either enhance or decrease the synthesis of MAG could be utilized. An example of such a slow release intrauterine vehicle can be found in Zhu et al. "The effect of intrauterine devices, the stainless steel ring, the copper T220, and releasing levonorgestrel, on the bleeding profile and the morphological structure of the human endometrium—a comparative study of three IUDs. A morphometric study of 96 cases," *Contraception* 40:425–38 (1989).

In another embodiment of the invention, endogenous MAG synthesis can be augmented in a mammal about the time the uterus of the mammal will be contacted with a conceptus whereby the chances of the conceptus becoming implanted in the uterus are enhanced. This method comprises administering to the mammal an agent which stimulates mammalian endometrial cells in culture to make MAG in an amount effective to augment MAG synthesis in the mammal.

Compounds found in the plasma, ECM, or maternal decidua of a mammal are expected to be useful for enhancing MAG synthesis Therefore, those compounds in plasma, extracellular matrix (ECM) extracts, or maternal decidua which induce MAG synthesis can be readily identified in an in vitro endometrial culture assay and employed in the method of this invention in an amount sufficient to augment MAG synthesis in a mammal. Such compounds are expected to include steroids and gonadotropins as well as other peptides, and glycopeptide hormones, growth factors, cytokines, antibodies, as well as portions of ECM proteins including fibronectins, laminin, collagen, entactin, vitronectin, or proteoglycans.

MAG synthesis can be augmented in a mammal about the time the uterus of the mammal will be contacted with a conceptus whereby the chances of the conceptus becoming implanted in the uterus are enhanced.

Thus, methods of increasing the probability that a conceptus will become implanted in a uterus, preferably by infusion of MAG or a compound that augments MAG synthesis in a mammalian uterus, are provided by this invention.

CONTRACEPTION AND CONTRAGESTION

In another aspect of this invention, a method of inhibiting MAG synthesis in a mammal is provided. The method comprises administering to said mammal a compound in an amount effective to inhibit MAG synthesis in said mammal which compound inhibits MAG synthesis by mammalian endometrial cells in culture.

Inhibition of MAG synthesis in a mammal has a variety of utilities. For example, a mammal determined to have a level of MAG in excess of a normal fertile control, may be a candidate for MAG inhibition. Additionally, MAG inhibition can be employed to a level where a method of contraception is provided. Additionally, MAG inhibition can be utilized to terminate a pregnancy and thus provide a method of contragestion.

An alternative approach to decrease mammalian MAG synthesis is antisense oligonucleotide inhibitors. Recently it has been demonstrated that adding oligonucleotide antisense DNA probes to cells causes them to specifically stop producing the corresponding messenger RNA. See e.g., Tortora et al., "An antisense oligodeoxynucleotide targeted against the type II beta regulatory subunit mRNA of protein kinase inhibits cAMP-induced differentiation in HL-60 leukemia cells without affecting phorbol ester effects," *Proc Natl Acad Sci U S A* 87:705–8 (1990).

An antisense oligonucleotide specific for MAG can readily be made and be given to a mammal in a variety of ways For example, the antisense oligonucleotide could be given parenterally via intravenous injection, in slow release form in the subcutaneous tissues, or as a slow release form in a gel or sponge applied to the cervix or intrauterine cavity in an amount sufficient to inhibit MAG secretion in the endometrium. Treatment with an antisense oligonucleotide specific for MAG is expected to only prevent the synthesis of MAG, and should not have any untoward systemic effects.

In another aspect of this invention, a method of decreasing free MAG (i.e., MAG being unbound to an antibody) in a mammal is provided comprising administering to the mammal MAG antibodies sufficient to bind to at least some MAG in the mammal.

In place of the pharmacologic and biochemical manipulation to decrease MAG synthesis described herein, this method applies, either locally or systemically, specific mammalian antibodies against MAG to provide reduction in the levels of free MAG. This is expected to serve a similar function as decreasing MAG synthesis since the antibodies could compete directly with the binding for MAG. Once this binding is inhibited by the anti-MAG antibodies, implantation could not take place. Human anti-MAG monoclonal antibodies, prepared by methods known to those in the art, are expected to have advantages over the murine monoclonal antibodies in the method of the invention, in that there is a much lower incidence of immune reaction to the humanized form of antibodies. The purified MAG antigen for development of these antibodies can be readily prepared by standard biochemical means from cultured endometrial conditioned media.

Immunologic interruption of pregnancy has been achieved. For example, it has been shown that when 5 and 25 mg of purified anti-hCG was injected into three patients with ectopic pregnancies, one of these patients completely resolved their tubal pregnancy, while the two others had markedly decreased levels of progesterone and estrogen, suggesting a marked decrease in viability of the pregnancy. Frydman et al., "Phase I clinical trial of monoclonal anti-human chorionic gonadotropin antibody in women with an ectopic pregnancy," *Fertil Steril* 52:734–8 (1989). These authors used mouse monoclonal antibodies. In a more recent article using human monoclonal antibodies, it was shown that humanized antibodies could be utilized in the treatment of CMV after renal transplantation. Skarp et al., "Use of a human monoclonal anti-cytomegalovirus antibody for the treatment of severe cytomegalovirus after renal transplantation," *Transplant Proc* 22:234 (1990). Finally, the general advantages of human monoclonal antibodies over mouse monoclonal antibodies has been described. Ehrlich et al., "Human and primate monoclonal antibodies for in vivo therapy," *Clin Chem* 34:1681–8 (1988).

In addition to being given systemically, it is believed these particular antibodies could also be applied directly within the intrauterine cavity and possibly within the fallopian tube.

In another aspect of this invention, a method of sterilizing a mammal is provided. By the method of this invention, a mammal is sterilized by administering to the mammal a MAG antigen in an amount sufficient to raise antibodies to MAG, whereby the probability that a conceptus will become implanted in the uterus in decreased.

Since MAG appears in the early secretory endometrium, a novel method of permanent female sterilization based on MAG immunization is provided. These antibodies would bind to MAG secreted by the mammal endometrial.

Mammals could be immunized against MAG by using MAG, antigenic portions thereof, with or without agents known to those in the art attached thereto to increase the antigenic potential of the antigen. Generally the protein can be dissolved at between about 1 to 50 μg/ml in sterile saline or saline with 0.4 mg aluminum hydroxide per ml as a vehicle. Generally 0.5 to 1.0 ml of the protein solution is injected intramuscularly and then followed by booster injections at one and 6–12 months after the initial immunization.

There is precedence for immunizing patients and animals against various products of pregnancy to induce contraception. For example, 88 subjects which were immunized with a β-hCG base vaccine have been investigated. Kharat et al., "Analysis of menstrual records of women immunized with anti-hCG vaccines inducing antibodies partially cross-reactive with hLH," *Contraception* 41:293–9 (1990) In animals, it has been shown that antibodies made against pig zonae pellucidae could induce contraception in mares. Liu et al., "Contraception in mares heteroimmunized with pig zonae pellucidae," *J Reprod Fertil* 85:19–29 (1989). Finally, in a study in dogs, it has been shown that contraception could be induced by immunizing dogs against gonadotropin releasing hormone. Gonzalez et al., "Immunological approaches to contraception in dogs," *J Reprod Fertil Suppl* 39:189–98 (1989).

SECRETORY FUNCTION OF EXOCRINE TISSUES

It has been recognized that MAG reactivity as demonstrated by immunohistochemistry is present in a variety of other tissues in the human body. In other words, the antibody found in mouse ascites also stains at least the Golgi bodies of the following tissues in addition to the endometrium. These tissues consist mostly of a number of tissues which are part of the exocrine glands (glands which secrete products into ducts) of the body, for example; lacrimal glands, pancreas, prostate, salivary glands, and sweat glands. In addition, the following tissues also have been recognized to exhibit MAG reactivity by immunohistochemistry; gall bladder epithelium and bile ducts, seminal vesicles and cervical glands. Thus, MAG is believed to represent a marker of secretory function in these cells. Hence, cells which contain normal MAG reactivity (i.e., staining of the Golgi of a particular cell) would be considered to be a normal secretory cell. Cells which normally should contain MAG reactivity but do not stain with antibodies against MAG would be judged "secretory defective".

Accordingly, in another aspect of this invention, a means to determine secretory function of mammalian exocrine cells is provided. The method assesses the relative function of the exocrine tissue of a mammal by sampling the tissue and assaying the sample for MAG, whereby relatively greater concentrations of MAG are indicative of a higher secretory function of that tissue.

Tissue biopsies can be performed by a variety of techniques known to those skilled in the art and is an example of tissue sampling.

Assays for MAG are as previously described.

Accordingly, the method of the invention, markedly enhances the information gathered from tissue samples by actually assessing whether the mammal is making MAG, which is a measure of the secretory potential of that tissue. Mammals with abnormal secretory function could then be candidates for MAG manipulation as described previously. In addition to qualitatively assessing the amount of MAG, it is believed computer image analysis can be utilized to quantitate the amount of MAG made per glandular cell or glandular group or per whole tissue to give at least a semi-quantitative estimate of overall secretory potential for that tissue of the mammal being assessed.

Further provided by the invention, is a method of assessing the secretory function of a tissue by providing a sample of a bodily fluid secreted from the tissue or which had been in contact with the particular tissue from the mammal and assaying the sample for MAG, whereby relatively greater concentrations of MAG are indicative of a higher secretory function of the tissue. Examples of suitable fluids include tears, saliva, semen, cervical aspirates, sweat, and bile fluid and pancreatic secretions derived from percutaneous or endoscopic directed aspiration of the common bile duct and pancreatic ducts.

Assays for MAG are as described previously.

The methods of this invention, wherein MAG is assessed in a variety of tissues and the secretions of these tissues are then generally expected to be useful as diagnostic screens for secretory function in mammals suspected of having defects in any of these tissues. For example, a variety of patients have defects in the ability to secrete normal amounts of tears, sweat, seminal fluids, pancreatic fluids, biliary fluids, cervical fluid and saliva. In addition to having defects in the amounts of these secretions, other patients may have defects in the composition of these secretions. MAG screening is therefore expected to be useful in following patients who are undergoing treatments that attempt to improve the secretory function of these tissues.

METHOD OF PRODUCING MAG

MAG can be produced for uses such as those described herein by culturing normal or malignant mammalian endometrial glandular cells for a time sufficient to produce at least some MAG and separating the MAG thus produced by techniques known to those in the art. If desired, the amino acid sequence and DNA sequence of MAG can be readily determined by methods known to those in the art. Briefly, to obtain the amino acid sequence, a DNA molecule is synthesized which encodes a partial amino acid sequence of MAG or which represents the complementary DNA strand to such a DNA molecule which encodes a partial amino acid sequence. This synthetic DNA molecule may then be used to probe for DNA sequence homology in DNA sequences derived from the genomic DNA of the mammal or derived from cDNA copies of mRNA molecules isolated from the mammal. Generally, DNA molecules of fifteen (15) nucleotides or more are required for unique identification of homologous DNA. The number of different DNA molecules which can encode the amino acid sequence may be very large since each amino acid may be encoded for by up to six (6) unique trinucleotide DNA sequences or codons. Therefore, it is impractical to test all possible synthetic DNA probes individually and pools of several such DNA molecules can be used concomitantly as probes. The production of such pools which are referred to as "degenerate" probes is well known in the art. While only one DNA molecule in the probe mixture will have an exact sequence homology to the gene of interest, several of the synthetic DNA molecules in the pool may be capable of uniquely identifying the gene since only a high degree of homology is required.

One technique to identify a gene sequence employs the Polymerase Chain Reaction (PCR). See e.g., U.S. Pat. Nos. 4,683,195 and 4,683,202 which patents are incorporated by reference as if fully set forth herein. Essentially PCR allows the production of a selected DNA sequence when the two terminal portions of the sequence are known. Primers, or oligonucleotide probes, are obtained which correspond to each end of the sequence of interest. Using PCR, the central portion of the DNA sequence is then synthetically produced.

In one such method of employing PCR to obtain the gene, RNA is isolated from the mammal and purified. A deoxythymidylate-tailed oligonucleotide can then be used as a primer in order to reverse transcribe the RNA into cDNA. A synthetic DNA molecule or mixture of synthetic DNA molecules as in the degenerate probe described above is then prepared which can encode the amino-terminal amino acid sequence of the enzyme as previously determined. This DNA mixture is used together with the deoxythymidylate-tailed oligonucleotide to prime a PCR reaction. Because the synthetic DNA mixture used to prime the PCR reaction is specific to the desired mRNA sequence, only the desired cDNA will be effectively amplified. The resultant product represents an amplified cDNA which can be ligated to any of a number of known cloning vectors.

Finally, the produced cDNA sequence can be cloned into an appropriate vector using conventional techniques, analyzed and the nucleotide base sequence determined. A direct amino acid translation of these PCR products will reveal that they corresponded to the complete coding sequence for MAG.

In addition to obtaining MAG from endometrial culture, it is believed MAG can be more efficiently prepared using any of numerous well known recombinant techniques. Briefly, most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

The most commonly used procaryotes system for the production of recombinant proteins remains *E. coli*, however, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. Commonly used procaryotic control sequences include promoters for transcription initiation, optionally with an operator, along with ribosome binding site sequences.

A wide variety of eucaryotic hosts are also now available for production of recombinant foreign proteins. As in bacteria, eucaryotic hosts may be transformed with expression systems which produce the desired protein directly, but more commonly, signal sequences are provided to effect the secretion of the protein. Eucaryotic systems have the additional advantage that they are able to process introns which may occur in the genomic sequences encoding proteins of higher organisms. Eucaryotic systems also provide a variety of processing mechanisms which result in, for example, glycosylation, oxidation or derivatization of certain amino acid residues, conformational control, and so forth.

Commonly used eucaryotic systems include yeast, insect cells, mammalian cells, avian cells, and cells of higher plants. The list is not exhaustive. Suitable promoters are available which are compatible and operable for use in each of these host types as well as are termination sequences and enhancers, as e.g. the baculovirus polyhedrin promoter. As above, promoters can be either constitutive or inducible. For example, in mammalian systems, the MTII promoter can be induced by the addition of heavy metal ions.

The particulars for the construction of expression systems suitable for desired hosts are known to those in the art. For recombinant production of the protein, the DNA encoding it is suitably ligated into the expression system of choice, and the system is then transformed into the compatible host cell which is then cultured and maintained under conditions wherein expression of the foreign gene takes place. MAG thusly produced is recovered from the culture, either by lysing the cells or from the culture medium as appropriate and known to those in the art.

Correct ligations for plasmid construction can be confirmed by first transforming a suitable host with the ligation mixture. Successful transformants are selected by ampicillin, tetracycline or other antibiotic resistance or using other markers depending on the mode of plasmid construction, as is understood in the art.

MAG, which includes antigenic fragments thereof, thus produced can be injected into mice or other animals for the generation of an antibody response and the preparation of many different monoclonal antibodies to MAG by known techniques. See e.g., "Antibodies, A Laboratory Manual," Cold Spring Harbor (1988). Once anti-MAG antibodies are generated, as described above, those antibodies which specifically bind to MAG, but not other proteins or factors can readily be identified.

EXAMPLES

Example 1

MAG reactivity with normal human endometrial tissue.

A full series of human endometria (104 specimens) were subsequently analyzed for immunohistochemical staining with mouse ascites. This set of experiments revealed that a MAG reactive factor, MAG, first appears within the cytoplasm of endometrial epithelial cells in the mid-proliferative stage (~days 8–9), peaks and is secreted during days 16–17, then is quickly lost from the cells at about day 18. In addition, microvillous staining of the surface epithelial layer was identified in day 17–18 specimens. No MAG staining was noted in later secretory stages. MAG is critical to human reproduction, since endometrial secretion of this protein occurs during a very specific window, one to three days after ovulation.

In those specimens that possessed staining, the pattern was very specific: staining appeared in a perinuclear and apical pattern in epithelial cells of the endometrium, suggesting Golgi and secretory vesicle staining. Furthermore, staining was seen both within the glands of the endometrium, and within the surface epithelium, where implantation is believed to occur.

Example 2

Immunoblotting of human endometrium with anti-MAG antibodies 0.90 grams of day 16 endometrium was curetted from a fresh hysterectomy specimen, carried to the laboratory in Dulbecco's Modified Eagles' Medium (DMEM) containing 25 mM glucose and 25 mM HEPES (DMEM-HG) supplemented with gentamicin (50 μg/ml), glutamine (4 mM), and 20% (v/v) heat-inactivated fetal calf serum. The tissue was then placed into 5 ml of four-times concentrated loading buffer (containing 250 mM Tris, pH 6.8, 40% glycerol, 8% SDS, 0.02% bromophenol blue, and 2.5% DTT), homogenized for 2 minutes and 45 seconds on ice with a Brinkman Homogenizer, model PT 15/35 at a setting of 3.5. The homogenate was placed in several Eppendorf vials, centrifuged with a Savant table top centrifuge for 5 minutes at 10,000 RPM. 10, 25, 50 and 100 μl of the resultant supernatant (diluted with 30, 75, 150 and 300 μl deionized water) was electrophoresed on a 10% SDS-PAGE gel under reducing conditions. The gel was electrotransferred to nitrocellulose (Schleicher and Schull) overnight, incubated with control hybridoma supernatant and two mouse ascites samples, both diluted 1:500. Antigen bands were identified with immunodetection using a biotinylated anti-mouse secondary antibody (ABC Vectastain, Vector Labs, Burlingame, Calif.).

A variety of strains of mice, both normal and immunized, yielded ascites fluid with antibodies for MAG. One such mouse strain was a first generation cross from $CB6F_1/J$ with C57 black/BALB/c.

The control hybridoma resulted in a number of non-specific bands. Both ascites produced new bands at approximately 42 kD and 200 kD. We conclude that the MAG factor represents either one or both of these newly identified protein bands.

What is claimed is:

1. A method of diagnosing the relative receptivity of the endometrium of a human to implantation of a conceptus, comprising:

obtaining a sample from the endometrium of said human at about one to three days after ovulation would be expected to occur;

contacting said sample with detectably labeled endogenous antibody of mouse ascites whereby antibody which binds to said endometrium sample is evidenced by detectable signal;

detecting signal associated with the binding of said endogenous antibody to said sample wherein detecting signal equal to or greater than that of a fertile control indicates a greater probability that the endometrium of said human will be receptive to implantation of a conceptus.

* * * * *